United States Patent
Li et al.

(10) Patent No.: US 9,797,007 B2
(45) Date of Patent: Oct. 24, 2017

(54) MICRO-LIQUID PHASE REACTION METHOD BASED ON SUBSTRATE WITH HYDROPHILIC-HYDROPHOBIC PATTERNED SURFACE

(71) Applicant: Suzhou Institute of Nano-Tech and Nano-Bionics of Chinese Academy of Science, Suzhou (CN)

(72) Inventors: Jiong Li, Suzhou (CN); Kexiao Zheng, Suzhou (CN)

(73) Assignee: Suzhou Institute of Nano-Tech and Nano-Bionics of Chinese Academy of Science, Suzhou (CN)

( * ) Notice: Subject to any disclaimer, the term of this patent is extended or adjusted under 35 U.S.C. 154(b) by 402 days.

(21) Appl. No.: 14/429,979

(22) PCT Filed: Nov. 30, 2012

(86) PCT No.: PCT/CN2012/001605
§ 371 (c)(1),
(2) Date: Mar. 20, 2015

(87) PCT Pub. No.: WO2014/082190
PCT Pub. Date: Jun. 5, 2014

(65) Prior Publication Data
US 2015/0225772 A1    Aug. 13, 2015

(51) Int. Cl.
*C12P 19/34* (2006.01)
*C12Q 1/68* (2006.01)
*B01J 19/00* (2006.01)
*B01L 3/00* (2006.01)

(52) U.S. Cl.
CPC .......... *C12Q 1/686* (2013.01); *B01J 19/0046* (2013.01); *B01L 3/5088* (2013.01); *B01J 2219/00596* (2013.01); *B01J 2219/00599* (2013.01); *B01J 2219/00619* (2013.01); *B01J 2219/00659* (2013.01); *B01J 2219/00722* (2013.01); *B01L 2200/12* (2013.01); *B01L 2300/161* (2013.01)

(58) Field of Classification Search
USPC ............................................... 435/6.12, 91.2
See application file for complete search history.

(56) References Cited

U.S. PATENT DOCUMENTS

| | | | |
|---|---|---|---|
| 2005/0003521 A1 | 1/2005 | O'Connor | |
| 2010/0184020 A1 | 7/2010 | Beer | |
| 2014/0018263 A1* | 1/2014 | Levkin | C12N 11/08 506/26 |
| 2014/0378339 A1* | 12/2014 | Lammertyn | B01L 3/502707 506/9 |

FOREIGN PATENT DOCUMENTS

| | | |
|---|---|---|
| CN | 2386437 Y | 7/2000 |
| CN | 1710103 A | 12/2005 |
| CN | 201770704 U | 3/2011 |

OTHER PUBLICATIONS

International Search Report of PCT application CN2012/001605.

* cited by examiner

*Primary Examiner* — Kenneth Horlick
(74) *Attorney, Agent, or Firm* — Wang Law Firm, Inc.

(57) ABSTRACT

A micro-liquid phase reaction method based on a substrate with a hydrophilic-hydrophobic patterned surface, including the following: applying a liquid phase system containing a hydrotropic substance and/or an amphipathic substance to a hydrophobic smooth plane in a sample-spotting manner to form an array of tiny droplets, subsequently removing the solvent in each droplet to bond the hydrotropic substance and/or amphipathic substance in each droplet to the hydrophobic smooth plane so as to form an array of hydrophilic bonding points, then moving an aqueous phase system or hydrophilic liquid phase system containing more than one reactants over the hydrophobic smooth plane, thereby forming island-like tiny reaction droplets at each hydrophilic bonding point, and finally under the set reaction conditions, reacting the reactants in each tiny reaction droplet. The method allows a parallel processing system for multiple reactions to be implemented under common experiment conditions, and greatly extends the application range thereof.

22 Claims, No Drawings

MICRO-LIQUID PHASE REACTION METHOD BASED ON SUBSTRATE WITH HYDROPHILIC-HYDROPHOBIC PATTERNED SURFACE

RELATED APPLICATION

This application claims the benefit of Chinese patent application, CN 201210499954.2, filed on Nov. 30, 2012, and PCT application WO/2014/082190 A1, filed on Nov. 30, 2012, the specifications of which are incorporated herein by this reference.

FIELD OF THE INVENTION

The present invention relates particularly to a micro-liquid phase reaction method based on a substrate with a hydrophilic-hydrophobic patterned surface, which is applied to the fields of biology, chemistry, medicine, material science, etc.

BACKGROUND OF THE INVENTION

In the field of research and industry with biological and chemical reactions as the basic experiment form, in order to obtain optimal results or products, a great number of reaction parameters are screened on a large scale, or multiple detections of different components of a sample are carried out. As the quantity of the required reactions is far beyond that of the reactions operated manually, an automatic parallel processing system for multiple reactions becomes a standard technical tool for this application.

In most applications, most macro-reaction parameters of all the reactions such as temperature and pressure are coincident (they may be time-varying), and the difference between the reactions mainly lies in the chemical substances taking part in reactions. Especially for a large number of biomedical detection applications, different indexes of a sample are determined by adding different reactants into a reaction system. So under many conditions, the parallel processing system for multiple reactions mainly solves the problems of how to add and isolate components of different reactions.

Currently, one known form of such detection device is a microtiter plate/microwell plate. It basically has a solid flat plate with a plurality of wells, and each well on the plate has a unique mark, and is used for storing a sample solution to be detected. For multiple reactions, the general practice is to add different reaction solutions into different wells. As the solution in each well is physically isolated, the reaction processes (hence their products or signals) do not interfere with each other, the end-point results of all the reactions may be read by a special detection instrument (or the entire reaction process is real-time monitored), and accordingly, this device may realize the parallel processing of multiple reactions.

But the defects of the microtiter plate/microwell plate at least lie in:

First, low reaction throughput. According to the general technical standards, a typical microtiter plate may have 6, 24, 96, 384 or 1536 wells. That is, a single microtiter plate maximally performs 1536 parallel reactions. For a classic microtiter plate/microwell plate, to increase its throughput may be achieved just by using much more microtiter plates/microwell plates, but higher cost of the microtiter plate/microwell plate results in high detection cost.

Second, large sample consumption. When the existing microtiter plate/microwell plate is used for detection, each well generally needs a solution volume of tens to hundreds microliter ($\mu L$). This results in substantial difficulty in many biological or medicinal researches whose samples are extremely limited and too valuable to be disposed in a single-use manner.

Third, complicated sample-adding technology. For the microtiter plate/microwell plate, sample adding refers to the process of adding a certain volume of sample solution into each microwell. As the design of the microtiter plate is unbeneficial for locating a certain microwell in the array by a human operator, mistakes are easily made during manual adding of samples into a microtiter plate with 96 wells or above, so an automatic liquid transferring system is generally needed. However, this sample adding robot specially made for the microtiter plate is generally expensive and operated complicatedly, thus the cost of the entire detection process is increased.

Forth, high fabrication cost. One microtiter plate/microwell plate meeting the industrial standards has strict requirements for the properties such as mechanical, optical, chemical and surface properties, etc., and the structural size of the microtiter plate/microwell plate must guarantee enough processing precision on the premise of meeting above requirements. These lead to no significant reduction of its fabrication cost in the long-term application history of the microtiter plate/microwell plate.

As mentioned above, under many conditions, the difference between multiple reactions lies in the substances taking part in the reactions; one feasible technical approach is to store unique components of each reaction in independent reaction vessels (labeled or recorded for differentiation) but to add the same components in all the reaction vessels. The U.S. Company BioTrove developed an OpenArray® multi-well plate based on this technical approach, structurally, the OpenArray plate is a solid flat plate with multiple cylindrical wells, and the number of its wells are about 2000-3000. The inner surfaces of all the wells are chemically treated to be hydrophilic, but two opposite surfaces of the flat plate connected by the wells are hydrophobic. A matched automatic sample adding system is used to add unique reaction components into each well in advance. But the common reaction components to all the reactions (for example, the sample solution to be detected) may be added into all the wells once by a special sample adding instrument. After sample adding is finished, the reaction in each well depends on the reaction components added in advance, thus the parallel processing of multiple reactions is achieved. Compared with the traditional microtiter plate/microwell plate, the OpenArray detection flat plate has a plurality of advantages, for example, the manufacture process is simple, the limitations on the light transmission performance of the plate material are relatively loose, adding samples by directly immersing the entire plate in the sample solution and then taking the plate out allows no use of an expensive special sample adding device, etc. But when used for high-throughput detection, the OpenArray technique also has some defects, for example, adding all the 3072 wells needs about 100 $\mu L$ sample solution calculated according to about 33 nanoliters (nL) of liquid per well, and its sample consumption is larger. Furthermore, above results are obtained by using a special microfluid sample adding device developed for the OpenArray flat plate. Sample adding by the immersion method needs tens to hundreds of milliliters (mL) of solution. In addition, adding unique compound components of each reaction in advance into micro-wells is difficult, specially speaking, accurately adding these compounds into the micro-wells needs accurately adjusting the position of a spotting needle, which leads to expensive fabrication cost of the sample adding system; and the design of the throughput is limited by the precision of the sample pre-adding system. Meanwhile, the array of micro-wells must be machined precisely (even smaller position deviation caused by technical errors will lead to difficult spotting), thereby increasing the cost in a further aspect.

The U.S. Company Fluidigm developed another Dynamic Array or Digital Array integrated fluid circuit for dispensing and adding of sample solutions. With this technique precise automatic control of high-throughput detection process may be achieved. The throughput range of its product lines at present are approximately 2000-37000 parallel reactions/chips, and the volume range of the samples required is 10-0.85 nL per reaction, accordingly, its maximal throughput and minimal sample volume required by a single reaction are superior to those required by the OpenArray plate. However, the microfluid chip has complicated design and extremely high requirements for manufacture process. Moreover, the assay procedure requires expensive and dedicated instrumentation such as special sample adding and detection devices.

SUMMARY OF THE INVENTION

The objective of the invention is to provide a micro-liquid phase reaction method based on a substrate with a hydrophilic-hydrophobic patterned surface so as to overcome the defects in the prior art.

Generally speaking, to achieve above objective, one embodiment of the invention provides a solid substrate, one smooth surface of the solid substrate is used as the reaction face and the surface tension of the reaction face is made to be in differential distribution (pattern) so as to realize the automatic distribution of liquid phase systems of different polarities on the reaction face to form multiple tiny liquid phase reaction systems of discrete distribution (for example, array distribution), thereby constructing a parallel processing system for multiple reactions.

As the first embodiment of the invention, the reaction face of the solid substrate may have a continuous large hydrophobic region (preferably, its hydrophobicity allows a water phase system to move freely over the reaction face without leaving any residual droplets or layers), the remaining small hydrophilic region is spatially divided by the hydrophobic region into a great number of tiny island-shaped hydrophilic spots of uniform size, all the hydrophilic spots form a regular distribution on the reaction face, which is also called a reaction array, and unique reactants of each reaction condition exist on the surface of each hydrophilic spot.

A preferred embodiment of the invention may comprise the following steps:

(1) providing a substrate at least a part of whose surface area is a hydrophobic smooth plane, and applying a first liquid phase system at least containing a hydrophilic substance and/or an amphipathic substance to a hydrophobic smooth plane to form an array of tiny droplets;

(2) subsequently removing the substances with larger volatility than the set reference value in each tiny droplet to bond at least a part of the hydrophilic substance and/or the amphipathic substance or at least a part of the hydrophilic substance and/or the amphipathic substance and other substances with smaller volatility than the set reference value in each tiny droplet to the hydrophobic smooth plane so as to form an array of hydrophilic bonding points;

(3) then moving a second liquid phase system which is an aqueous phase system or a hydrophilic liquid phase system over the hydrophobic smooth plane to render the second liquid phase system automatically congregate at each hydrophilic bonding point to form tiny reaction droplets; and (4) Finally under the set reaction conditions, reacting the reactants all of which come from the second liquid phase system or simultaneously from the first liquid phase system and the second liquid phase system in each tiny reaction droplet.

However, for some reactions required to be performed in an oil phase system, it is apparent that those skilled in the art will be readily aware of the second embodiment of the invention according to the foregoing embodiment, that is, the reaction face of the solid substrate is made to have a continuous large hydrophilic region (similarly, its hydrophobicity shall be enough to allow an oil phase reaction system to move freely over the reaction face without remain), the remaining small hydrophobic region is spatially divided by the hydrophilic region into a great number of tiny island-shaped hydrophobic spots of uniform size (i.e. forming a tiny liquid phase reaction array), and similarly, unique reactants of each reaction condition exist on the surface of each hydrophobic spot. Accordingly, those skilled in the art may also adopt similar operations to obtain the second embodiment by referring to the preferred scheme of the first embodiment.

DETAILED DESCRIPTION OF THE PREFERRED EMBODIMENTS

As mentioned above, the existing parallel processing system for multiple reactions generally has one or a plurality of the problems of high chip cost, limited reaction throughput, large sample consumption, complicated sample-adding technique, expensive sample-adding equipment, etc, in view of this, the inventor of the invention puts forward the technical scheme of the invention based on long-term research and a large amount of practice, thereby solving the technical bottlenecks expected to be overcome by those skilled in the art for long term, allowing a parallel processing system for multiple reactions to be implemented under common experiment conditions, and greatly extending the application range thereof.

A preferred embodiment of the invention may comprise the following steps:

(1) providing a substrate at least a part of whose surface area is a hydrophobic smooth plane, and applying a first liquid phase system at least containing an hydrophilic substance and/or an amphipathic substance to a hydrophobic smooth plane to form an array of tiny droplets;

(2) subsequently removing the substances with larger volatility than the set reference value in each tiny droplet to bond at least a part of the hydrophilic substance and/or the amphipathic substance or at least a part of the hydrophilic substance and/or the amphipathic substance and other substances with smaller volatility than the set reference value in each tiny droplet to the hydrophobic smooth plane so as to form an array of hydrophilic bonding points;

(3) then moving a second liquid phase system which is an aqueous phase system or a hydrophilic liquid phase system over the hydrophobic smooth plane to render the second liquid phase system automatically congregate at each hydrophilic bonding point to form tiny reaction droplets; and (4) Finally under the set reaction conditions, reacting the reactants all of which come from the second liquid phase system or simultaneously from the first liquid phase system and the second liquid phase system in each tiny reaction droplet.

As one of embodiments, in the step (1), the first liquid phase system is applied to the hydrophobic smooth plane by any of spraying or spotting manners to form the array of tiny droplets.

Further, the spraying or spotting manners may be implemented by any of a needle type spotting instrument, an ink-jet spotting instrument and an ink-jet printer, but not limited to these.

As one of preferred embodiments, in the array of tiny droplets formed in the step (1), the size of each tiny droplet may be 0.1-900 μm, and the distance between adjacent tiny droplets may be 0.1-900 μm.

As one of embodiments, the first liquid phase system adopts any of an aqueous phase system, an oil phase system and an oil-water two-phase system.

As one of embodiments, in the step (2), in a natural evaporation manner or a controlled evaporation manner, the substances with larger volatility than the set reference value in each tiny droplet are removed completely, wherein the controlled evaporation manner may be implemented under the external conditions of heating, pressure reduction, etc, which may be selected and adjusted appropriately by those skilled in the art according to actual requirements.

As one of embodiments, the hydrophilic substance and/or the amphipathic substance in the step (2) is bonded to the hydrophobic smooth plane in a reversal physical absorption manner and/or a reversal chemical bonding manner.

As one of embodiments, in the steps (1)-(2), at least one of the hydrophilic substance and/or the amphipathic substance is a reactant taking part in the reaction of the step (4).

As one of embodiments, besides at least a hydrophilic substance and/an amphipathic substance, the first liquid phase system further contains one or more than one reactant for taking part in the reaction of the step (4).

As one of preferred embodiments, in the step (3), the droplet-shaped second liquid phase system may be dragged to slide across the hydrophobic smooth plane treated in the step (2) along the set path so as to automatically congregate at each hydrophilic bonding point to form tiny reaction droplets.

As one of preferred embodiments, the volume of the second liquid phase system may be 1-30 μL.

As one of embodiments, the step (4) may comprise

I. wrapping each tiny droplet by using an involatile oil phase substance not reacting with any of the reactants in the tiny droplet; and II. Setting the PCR reaction conditions to react the PCR reactants in each tiny reaction droplets mutually.

As one of application examples of the invention, the micro-liquid phase reaction method based on a substrate with a hydrophilic-hydrophobic patterned surface may be a PCR method, comprising the following steps:

(1) providing a substrate at least a part of whose surface area is a hydrophobic smooth plane, and applying a first liquid phase system at least containing a hydrophilic substance and/or an amphipathic substance taking part in the forming of a PCR reaction system to the hydrophobic plane in spraying and/or spotting manners to form an array of tiny droplets;

(2) subsequently removing the substances with larger volatility than the set reference value in each tiny droplet by evaporation to bond at least a part of the hydrotropic substance and/or the amphipathic substance or at least a part of the hydrotropic substance and/or the amphipathic substance and other substances with smaller volatility than the set reference value in each droplet to the hydrophobic smooth plane so as to form an array of hydrophilic bonding points;

(3) then moving a liquid phase system which contains other substances taking part in the forming of the PCR reaction system and is an aqueous phase system over the hydrophobic smooth plane to render the second liquid phase system automatically congregate at each hydrophilic bonding point so as to form tiny reaction droplets; and (4) Under the set PCR reaction conditions, reacting the PCR reactants in each tiny reaction droplet.

As one of embodiments, water in each tiny droplet formed by the first liquid phase system in the step (2) may be removed in a slow evaporation manner to separate solid solutes or solid solutes and solids and/or liquid substances with smaller volatility than water in each tiny droplet out to be absorbed on the hydrophobic smooth plane.

As one of embodiments, the second liquid phase may contain one or a plurality of a primer pair, a PCR template, polymerase and dNTP, certainly, may also contain various salts or additives, etc. required by the PCR reaction.

As one of preferred embodiments, in the array of tiny droplets formed in the step (1), the size of each tiny droplet is 0.1-900 μm, and the distance between adjacent tiny droplets is 0.1-900 μm.

As one of preferred embodiments, in the step (3), the droplet-shaped second liquid phase system of 1-30 μL may be dragged to slide across the hydrophobic smooth plane treated in the step (2) so as to automatically congregate at each hydrophilic bonding point to form tiny direction droplets.

As one of embodiments, the step (4) may comprise

I. wrapping each tiny droplet by using an involatile oil phase substance not reacting with any of the reactants in the tiny droplet; and II. Setting the PCR reaction conditions and reacting the PCR reactants in each tiny reaction droplets.

As another application example of the invention, the micro-liquid phase reaction method based on a substrate with a hydrophilic-hydrophobic patterned surface may be a PCR method shown as follows, comprising the following steps:

(1) providing a substrate at least a part of whose surface area is a hydrophobic smooth plane, and applying a primer pair aqueous solution containing at least one primer pair to the hydrophobic smooth plane so as to form an array of tiny droplets on the surface of the hydrophobic smooth plane;

(2) subsequently removing water in each droplet by slow evaporation to attach the primer pair or the primer pair and other solid solutes and/or components with smaller volatility than water to the hydrophobic smooth plane to form an array of hydrophilic bonding points;

(3) then sliding a sample template aqueous solution containing at least one sample template across the hydrophobic smooth plane to render the aqueous solution containing at least one sample template automatically congregate at each hydrophilic bonding point so as to form an array of tiny reaction droplets; and (4) wrapping each tiny droplet by using an involatile oil phase substance not reacting with any of the reactants in each tiny droplet, then setting the PCR reaction conditions and reacting the PCR reactants in each tiny reaction droplet.

As one of embodiments, the primer pair aqueous solutions have two kinds or above, and the primer pairs contained in each primer pair aqueous solution are different.

As one of embodiments, the primer pair aqueous solution further contains any one or a plurality of agarose, dextran, starch, polyethyleneglycol, serum protein and phospholipid, and may certainly contain other auxiliary agents such as salts, etc. required by the PCR reaction.

As one of embodiments, the aqueous solution of the sample template further contains any one or combination of more than two of DNA polymerase, dNTP, soluble salts required by the PCR reaction and a marking substance for indicating the occurrence of PCR reaction.

As one of embodiments, the marking substance for indicating the occurrence of PCR reaction may comprise a fluorescent probe, but is not limited to this.

As one of embodiments, the PCR method pertaining to the preferred embodiment may further comprise the following step:

(5) After the PCR reaction, measure the fluorescent signal of each reaction point in the array of tiny reaction droplets to complete the detection of target nucleic acid(s) in the sample.

The solid substrate may be made of various appropriate conventional materials known by those skilled in the art, and its form may be adjusted according to actual requirements. For example, as one of embodiments, the solid substrate may adopt a sheet structure, and its materials may be selected from silicon dioxide, polytetrafluoroethylen, polyvinylidene fluoride, polypropylene plastics, polyethylene plastics, polystyrene plastics, polyacrylamide membranes, silicone plastics, metals, ceramics, mica, etc, but are not limited to these.

Generally speaking, the solid substrate shall be first subjected to surface treatment before the reaction face is made. For example, for the first embodiment of the invention, the substrate made of hydrophobic materials may be generally washed by using an organic solvent and water in order, and then dried. The substrate made of hydrophilic materials or weak hydrophobic materials may be generally washed by using an organic solvent and water in order and then dried, and then a hydrophobic modifier is coated or deposited on the surface of the substrate to form a reaction face with a hydrophilic layer. The hydrophobic modifier may be selected from various conventional hydrophobic modifiers used by those skilled in the art, especially organic compounds with hydrophobic carbon chains, for example, substances containing hydrophobic carbon chains, including silicon-containing organic compounds, organic fluorine compounds, oxygen-bearing organic matters, chlorine-containing organic matters, nitrogenous organic matters or hydrocarbons such as silicon fluoride, chlorosilane, polypropylene, etc.

Accordingly, for the second embodiment of the invention, those skilled in the art may be readily aware of treating the materials and the reaction face of the solid substrate according to the inspiration of above ideas to meet actual application needs.

More specially, a typical embodiment of the invention may be implemented by the following scheme: first generating an array of hydrophilic spots on a highly hydrophobic surface by a controlled spotting step and rendering each spot contain corresponding reactant molecules.

Wherein all the array spots in the array of hydrophilic spots have the same shape and size, wherein as a preferred embodiment, the length of the plane FIGURE formed by a single array spot on any direction of the reaction face is maximally 0.1-900 μm, and the distance between most adjacent array spots is 0.1-900 μm.

The instruments for sample spotting may be selected from a commercial needle type spotting instrument, an ink-jet spotting instrument, an ink-jet printer, etc. Moreover, such sample spotting instruments may fetch different spotting solutions from more than one reservoir and then apply the spotting solutions to the specific positions on the reaction face set by a spotting program.

The solutions for spotting may comprise a reaction premix, a hydrophilic/an amphipathic compound and water, wherein the reaction premix shall contain unique substances to each reaction taking part in the reaction, for example, an initiator and a catalyst of inorganic reactions, or an antibody of immune reactions, or a primer of PCR reactions, etc., but is not limited to these. In addition, the reaction premix may further contain or not contain some common auxiliary substances to all reactions, such as a cosolvent, a stabilizer, a surfactant, etc, but is not limited to these.

The reaction premix may be bonded or absorbed to the surface of the plate covered by the spotting droplet during slow drying after spotting.

To change the property of surface tensions of the spotting point, the liquid for spotting may contain a certain amount of hydrophilic or amphipathic compound. Such compound may similarly be bonded or absorbed to the surface of the plate covered by the stopping droplet to be of hydrophilicity during slow drying after spotting.

For example, for some biochemical reaction systems, the hydrophilic or amphipathic compound may be any one or combination of carbohydrates such as agarose, dextran, starch, polyethyleneglycol, but is not limited to these; may also be any one or combination of amphapithic substances such as serum protein, synthesized amphapithic substances, phospholipids, etc, but is not limited to these.

Corresponding spotting solutions for different reactions are stored in different reservoirs in advance, are sequentially applied to the specific positions on the reaction face set by a spotting program by using a spotting instrument according to the preset program during spotting so as to form hydrophilic array spots formed by solutes separated out from different spotting solutions after drying. According to particular experiment requirements, the array spots may be different with each other, and alternatively may be same for each different reaction. By controlling the conditions of drying, the shape, the size and the height of each array spot may be uniform, and the deposited solutes are distributed uniformly on its surface.

After the array of hydrophilic spots is constructed, for loading main compositions (sample) common to all reactions, preferably, a single droplet of a 1-3 μL sample solution may be adopted to move over the reaction face, and its entire moving area shall cover a part or the complete of hydrophilic array spots. Due to the difference of surface tensions, the sample liquid will be kept only on the surfaces of the hydrophilic array spots after dragging. In this way, an array consisting of a large number of tiny droplets will be formed on the reaction face when the sample droplets complete sweeping the array area (at end of the movement, the droplet itself leaves the plate). After the array is formed, soluble reactant molecules absorbed on each hydrophilic array spot are gradually subjected to rehydration to enter the liquid phase to form a mixed solution with the sample. As each hydrophilic array spot has contained reactant compounds required by different reactions, and the corresponding reaction processes are limited inside the tiny droplets without interference with each other, a micro-volume multiple reaction system is built on the reaction face.

During the reaction process, the environmental humidity in proximity of the plate assembly is well-controlled to keep the evaporation of the droplets at minimal level so not to affect the reaction underway; alternatively, the reaction face may be put in some closed container, and then an oil phase liquid is added to wrap each tiny droplet to render the tiny droplet not move, evaporate and be mixed with each other, wherein the oil phase substance may be selected from silicone oil, hydrocarbons, chlorine-containing hydrocarbon, oxygen-containing hydrocarbon, fluorine-containing hydrocarbon, mineral oil (eneyne), etc, but is not limited to these.

After the reaction is over, the processing of multiple reactions of the sample is finished by measuring and analyzing the results of each reaction through some detectable signals such as fluorescent signals, chemiluminescent signals, electrochemical signals, etc.

The detectable signals may be generated by a marking substance contained in the reaction system, or spontaneously generated by the reactants during mutual reactions. For example, for the PCR reactions, the marking substance may be an independent fluorescent probe added in the reaction system, or a fluorescent probe combined onto a certain reactant therein, but is not limited to these.

Generally speaking, based on the elaboration of the specifications, those skilled in the art may be readily aware that the invention at least has the following advantages compared with the prior art:

(1) The throughput is high, for example, on a 75×25 mm substrate, more than $10^4$ points may be easily spotted according to the scheme of the invention, far beyond that of the current parallel processing systems for multiple reactions;

(2) The method is flexible, by selecting spotting solutions prepared in advance, different reactions may be conveniently carried out on the substrate with high efficiency;

(3) Micro-machining of the substrate is unnecessary, and the problem of aligning to the specific positions on the substrate during spotting does not exist, and the construction of a reaction array may be finished by using an existing common device (for example, a commercial printer);

(4) The reagent consumption and the sample consumption are reduced as the volume of tiny droplets required for the forming of tiny reaction reactions is small, and the density of the array is optimized accordingly; and (5) The materials of the substrate have no special requirements and may be selected from a wide range, special reaction instruments and/or detection instruments are unnecessary during assay procedure, and a conventional device may be used to finish the entire reaction process, and the cost is extremely low.

The technical scheme of the invention is set forth by combining a plurality of following preferred embodiments.

Embodiment 1

The embodiment relates to a multiple PCR reaction, comprising the following steps:

(1) A 75×25×1 mm glass slide is washed sequentially with acetone, ethanol, and pure water for five minutes each, subsequently subjected to ultrasonic washing with isopropanol for ten minutes and finally washed with pure water for twice, each for five minutes. The cleaned silicone sheet is blow dried by using nitrogen gas, (2) The silicone sheet is immersed in a 5% (v/v) silicon fluoride solution (the solvent is anhydrous toluene) for reaction for one minute, and then is washed in isopropanol and pure water sequentially for five minutes for each, (3) Different primers (oligonucleotide) required by each PCR reaction are formulated into a plurality of spotting solutions further containing 1% agarose and 1% BSA (bovine serum albumin), which is applied to the surface of the silicon sheet by using an automatic program-controlled spotting device to form a reaction array, appropriate spotting parameters are set so that the spotted points form a circle with the diameter of 100 μm after drying. The array is a 100×350 rectangle, and the distance between adjacent spotting points is 100 μm on the X direction and the Y direction, (4) The silicone sheet is firstly put in a humidity chamber (at 37° C. temperature and 50% humidity) for 4 hours so that various solute molecules in the spotting solution are absorbed or deposited onto the surface of the substrate, then the silicone sheet is kept in a dryer (at room temperature) for 3 hours for removing the moisture in the tiny spotting droplets, (5) A sample droplet to be amplified (containing a template nucleic acid molecule, a nucleotide monomer, polymerase, a fluorescent dye or TaqMan fluorescent probe, a buffer component and compounds for preventing water evaporation such as lycine, etc.) is dragged by using an appropriate device (a micropipettor, a capillary pipe, an injection needle, etc.) to move over the reaction face and to sequentially slide across all the reaction spots according to the set path. Due to the difference of surface tension, a certain volume of solution is remained on the surface of the reaction spot after the sample droplet slides over, but the hydrophobic part of the reaction face has no solution remaining. The reaction components left on the surface of the reaction spots, such as primer molecules, etc. enter the solution liquid phase due to rehydration. In this way, an array of multiple PCR reactions comprising a plurality of tiny droplets is formed, (6) The array of tiny droplets is wrapped with silicone oil (by sliding an appropriate amount of silicone oil across the array with an appropriate speed), (7) The PCR amplification is carried out on a PCR instrument compatible with the glass slide. The setting of the cyclic reaction program is determined according to the technical knowledge known in the industry, (8) The multiple reaction plate devices is taken out after the amplified reaction is over and loaded to a microarray scanner, and an appropriate excitation wavelength is selected according to the fluorescent dyes used to scan the surface of the sample array to obtain its fluorescence intensity distribution. The relative contents of the PCR amplified products may be determined according to the fluorescence intensity of each reaction spot, wherein the fluorescence intensity of the unamplified reaction spots is considerably lower than that of the amplified reaction spots.

This application mode is applicable to differentiation of specific sequences, for example, detection of mutation points, as this application need no precise quantitative fluorescent signals. As the controls have a negative control and a positive control, it is considered that the sample solution contains a template sequence that is complementary to the primer and provided with mutation points when the fluorescent signal of the reaction spot is close to that of the positive control, and those below the threshold value are considered as wild-type sequences.

Above specifications and embodiments shall not be construed as limiting the design ideas of the invention. A person in the art having the same knowledge may make various forms of improvements and modifications and changes of the technical ideas of the invention, and such improvements and modifications and changes shall be apprehended within the protection scope of the invention.

What is claimed is:

1. A micro-liquid phase reaction method based on a substrate with a hydrophilic-hydrophobic patterned surface, comprising the following steps:
   (1) firstly providing a substrate at least a part of whose surface area is a hydrophobic smooth plane, and applying a first liquid phase system at least containing a hydrophilic substance and/or an amphipathic substance to the hydrophobic plane to form an array of droplets;
   (2) subsequently removing any substances with larger volatility than a set reference value in each droplet to bond at least a part of the hydrophilic substance and/or the amphipathic substance or at least a part of the hydrophilic substance and/or the amphipathic substance and other substances with smaller volatility than the set reference value in each droplet to the hydrophobic smooth plane so as to form an array of hydrophilic bonding points;
   (3) then moving a second liquid phase system which is an aqueous phase system or a hydrophilic liquid phase system over the hydrophobic smooth plane to render the second liquid phase system automatically congregating at each hydrophilic bonding point so as to form reaction droplets; and
   (4) finally under set reaction conditions, reacting reactants which come from the second liquid phase system, or simultaneously from the first liquid phase system and the second liquid phase system in each reaction droplet.

2. The micro-liquid phase reaction method based on a substrate with a hydrophilic-hydrophobic patterned surface of claim 1, wherein in the step (1), the first liquid phase system is applied to the hydrophobic smooth plane in any of spraying or spotting manners to form an array of droplets.

3. The micro-liquid phase reaction method based on a substrate with a hydrophilic-hydrophobic patterned surface of claim 2, wherein the spraying or spotting manners are implemented by any of a needle type spotting instrument, an ink-jet spotting instrument and an ink-jet printer.

4. The micro-liquid phase reaction method based on a substrate with a hydrophilic-hydrophobic patterned surface of claim 1, wherein the size of each droplet in the array of droplets formed in the step (1) is 0.1-900 μm, and the distance between adjacent droplets is 0.1-900 μm.

5. The micro-liquid phase reaction method based on a substrate with a hydrophilic-hydrophobic patterned surface of claim 1, wherein the substances with larger volatility than the set reference value in each droplet is volatized completely in natural evaporation or controlled evaporation manners.

6. The micro-liquid phase reaction method based on a substrate with a hydrophilic-hydrophobic patterned surface of claim 1, wherein the hydrophilic substance and/or the amphipathic substance in the step (2) is bonded to the hydrophobic smooth plane in reversible physical absorption and/or reversible chemical bonding manners.

7. The micro-liquid phase reaction method based on a substrate with a hydrophilic-hydrophobic patterned surface of claim 1, wherein at least one of the hydrophilic substance and/or the amphipathic substance in the steps (1)-(2) is one of the reactants taking part in the reaction in the step (4).

8. The micro-liquid phase reaction method based on a substrate with a hydrophilic-hydrophobic patterned surface of claim 1, wherein besides the at least one hydrophilic substance and/or the amphipathic substance, the first liquid phase system further contains at least one reactant for taking part in the reaction in the step (4).

9. The micro-liquid phase reaction method based on a substrate with a hydrophilic-hydrophobic patterned surface of claim 1, wherein the second liquid phase system is dragged to slide across the hydrophobic smooth plane treated in the step (2) along a set path to automatically congregate at each hydrophilic bonding point so as to form the reaction droplets.

10. The micro-liquid phase reaction method based on a substrate with a hydrophilic-hydrophobic patterned surface of claim 9, wherein the volume of the second liquid phase system is 1-30 μL.

11. The micro-liquid phase reaction method based on a substrate with a hydrophilic-hydrophobic patterned surface of claim 1, wherein the step (4) comprises
   I. wrapping each droplet by using an involatile oil phase substance not reacting with any of the reactants in the droplet; and
   II. setting the reaction conditions and reacting the reactants in each droplet.

12. A PCR method, comprising the following steps:
   (1) firstly providing a substrate at least a part of whose surface area is a hydrophobic smooth plane, and applying a first liquid phase system containing at least a hydrophilic substance and/or an amphipathic substance taking part in the forming of a PCR system to a hydrophobic smooth plane in spraying and/or spotting manners so as to form an array of droplets;
   (2) subsequently removing any substances with larger volatility than a set reference value in each droplet by evaporation to bond at least a part of the hydrophilic substance and/or the amphipathic substance or at least a part of the hydrophilic substance and/or the amphipathic substance and other substances with smaller volatility than the set reference value in each droplet to the hydrophobic smooth plane so as to form an array of hydrophilic bonding points;
   (3) then moving a second liquid phase system which contains other substances taking part in the forming of the PCR system and is an aqueous phase system over the hydrophobic smooth plane to render the second liquid phase system automatically congregating at each hydrophilic bonding point so as to form reaction droplets; and
   (4) finally under set PCR reaction conditions, reacting PCR reactants in each reaction droplet.

13. The PCR method of claim 12, wherein in the step (2), water in each droplet formed by the first liquid phase system is removed in a controlled evaporation manner so as to separate solid solutes or solid solutes and solids and/or liquid substances with smaller volatility than water in each droplet out to be absorbed on the hydrophobic smooth plane.

14. The PCR method of claim 12, wherein the second liquid phase system at least contains any of a primer pair, a PCR template, a polymerase and dNTP.

15. The PCR method of claim 12, wherein the size of each droplet in the array of droplets formed in the step (1) is 0.1-900 μm, and the distance between adjacent droplets is 0.1-900 μm.

16. The PCR method of claim 12, wherein in the step (3), the second liquid phase system is dragged to slide across the hydrophobic smooth plane treated in the step (2) along a set path to automatically congregate at each hydrophilic bonding point so as to form reaction droplets.

17. The PCR method of claim 12, wherein the step (4) comprises

I. wrapping each droplet by using an involatile oil phase substance not reacting with any of the reactants in the droplet; and II. setting PCR reaction conditions and reacting the PCR reactants in each reaction droplet.

18. A PCR method, comprising the following steps:
(1) firstly providing a substrate at least a part of whose surface area is a hydrophobic smooth plane, and applying a primer pair aqueous solution containing at least one primer pair to a hydrophobic smooth plane so as to form an array of droplets on the surface of the hydrophobic smooth plane, each droplet having PCR reactants within;
(2) subsequently removing water in each droplet by controlled evaporation to attach the primer pair or primer pair and other solid solutes and/or components with smaller volatility than water to the hydrophobic smooth plane to form an array of hydrophilic bonding points;
(3) then sliding a sample template aqueous solution containing at least one sample template across the hydrophobic smooth plane to render the aqueous solution containing at least one sample template automatically congregating at each hydrophilic bonding point so as to form an array of reaction droplets; and
(4) wrapping each droplet by using an involatile oil phase substance not reacting with any of the PCR reactants in the droplet, setting PCR reaction conditions, and reacting the PCR reactants in each reaction droplet.

19. The PCR method of claim 18, wherein the primer pair aqueous solution further contains any one or combination of more than two of agarose, dextran, starch, polyethyleneglycol, serum protein and phospholipid.

20. The PCR method of claim 18, wherein the aqueous solution of the sample template further comprises any one or combination of more than two of DNA polymerase, dDNP, soluble salts required by the PCR reaction and a marking substance for indicating the occurrence of PCR reaction.

21. The PCR method of claim 20, wherein the marking substance for indicating the occurrence of PCR reaction comprises a fluorescent probe.

22. The PCR method of claim 18, the method further comprising the following step:
(5) detecting a fluorescent signal of each reaction point in the array of reaction droplets to achieve the detection of the sample template after the PCR reaction is finished.

* * * * *